(12) United States Patent
Boden et al.

(10) Patent No.: US 7,691,814 B2
(45) Date of Patent: Apr. 6, 2010

(54) OSTEOGENIC COMPOSITIONS COMPRISING AN AMINO ACID SEQUENCE CAPABLE OF BEING PHOSPHORYLATED BY CAMK2

(75) Inventors: Scott D. Boden, Atlanta, GA (US); Sreedhara Sangadala, Dallas, GA (US)

(73) Assignee: Emory University

( * ) Notice: Subject to any disclaimer, the term of this patent is extended or adjusted under 35 U.S.C. 154(b) by 0 days.

(21) Appl. No.: 11/633,963

(22) Filed: Dec. 5, 2006

(65) Prior Publication Data

US 2007/0191591 A1 Aug. 16, 2007
US 2009/0234100 A9 Sep. 17, 2009

Related U.S. Application Data

(63) Continuation-in-part of application No. 11/385,612, filed on Mar. 21, 2006, now Pat. No. 7,504,374, and a continuation-in-part of application No. 10/806,915, filed on Mar. 23, 2004.

(60) Provisional application No. 60/772,322, filed on Feb. 10, 2006, provisional application No. 60/456,551, filed on Mar. 24, 2003.

(51) Int. Cl.
*A61K 38/16* (2006.01)
*A61K 38/17* (2006.01)

(52) U.S. Cl. ............ 514/12; 514/2; 514/7; 514/8; 424/423; 523/113; 523/115

(58) Field of Classification Search .......... None
See application file for complete search history.

(56) References Cited

U.S. PATENT DOCUMENTS 5,888,223 A * 3/1999 Bray, Jr. ............... 623/17.16
5,935,594 A 8/1999 Ringeisen et al.
6,468,754 B1 * 10/2002 Greene et al. .............. 435/6
2004/0197867 A1 * 10/2004 Titus et al. ............. 435/69.1

OTHER PUBLICATIONS

Ignotz et al. (2005, Biology of Reproduction 73:519-526).*
Tong et al. (2004, J. Physiol. 558(Pt.3): 927-941).*
Wang et al. (1998, PNAS USA 95:7133-7138).*
Ackerman et al., "Economic evaluation of bone morphogenetic protein versus autogenous iliac crest bone graft in single-level anterior lumbar fusion", Spine 2002; vol. 27, No. 16S, pp. S94-S99.
Boden et al., "Lumbar spine fusion by local gene therapy with a cDNA encoding a novel osteoinductive protein (LMP-1)", Spine 1998; vol. 23, pp. 2486-2492.
Liu et al., "Overexpressed LIM mineralization proteins do not require LIM domains to induce bone", Journal of Bone and Mineral Research, 2002; Vol. 17, No. 3, pp. 406-414.
Boden et al., "LMP-1, a LIM-domain protein, mediates BMP-6 effects on bone formation", Journal of Endocrinology 1998; vol. 139, No. 12, pp. 5125-5134.
Créton et al., "Presence and roles of calcium gradients along the dorsal- ventral axis in drosophila embryos", Developmental Biology 2000; vol. 217, pp. 375-385.

* cited by examiner

*Primary Examiner*—Elizabeth C. Kemmerer

(57) ABSTRACT

Novel osteogenic compositions and methods are provided. In a broad aspect, the composition comprises either a first amino acid sequence which is capable of being phosphorylated by CAMK2; or a nucleic acid sequence encoding the first amino acid sequence; or a combination thereof. Optionally, the first amino acid sequence may further comprise a second amino acid sequence which is capable of binding the Smurf1 protein. Further, the composition may comprise a BMP protein and/or an agent capable of decreasing an amount or an activity of CAMK2. The compositions of the instant invention may be incorporated into an implant or delivered via a catheter.

6 Claims, No Drawings

OSTEOGENIC COMPOSITIONS COMPRISING AN AMINO ACID SEQUENCE CAPABLE OF BEING PHOSPHORYLATED BY CAMK2

CROSS-REFERENCE TO RELATED APPLICATIONS

This application is a continuation-in-part of U.S. application Ser. No. 11/385,612, filed on Mar. 21, 2006, now U.S. Pat. No. 7,504,374 which claims benefit of U.S. Provisional Application 60/772,322 filed on February 10, 2006. The teachings of both of these applications are incorporated herein by reference to the extent they are not inconsistent with the instant disclosure. This application is also a continuation-in-part of U.S. application Ser. No. 10/806,915, which was filed on Mar. 23, 2004, which claims benefit of U.S. Provisional Application Serial No. 60/456,551, filed on Mar. 24, 2003.

STATEMENT REGARDING FEDERALLY FUNDED RESEARCH

This invention was made with government support under Grant No. R01-AR53093 awarded by the National Institute of Health. The Government has certain rights in the invention.

FIELD OF INVENTION

This invention relates to compositions and methods for inducing osteogenesis.

BACKGROUND

Many Americans are afflicted by low back pain, degenerative spinal disease, or bone fractures. These musculoskeletal problems are responsible for a major portion of the health care budget and are among the greatest causes of chronic disability and lost productivity in the United States. Orthopaedic surgical treatment of these problems frequently requires bone grafting to promote healing. Fusion of two or more bones with cancellous bone graft may fail to heal in 25-45% of patients, and in even higher percentage of smokers and diabetic patients, co-morbidities which are more prevalent in the veteran population. Use of osteoinductive proteins such as BMP-2 to induce bone formation in these patients is now possible.

In 2002 the U.S. Food and Drug Administration approved rhBMP-2 for use as a bone graft substitute in interbody spine fusions. Despite this regulatory milestone for BMP-2, this technology is not feasible for many patients with bone healing needs due to an unexpectedly high dose required in humans which has resulted in a very high cost (Boden S D, Zdeblick T A, Sandhu H S, and Heim S E. *Spine* 2000; 25:376-81; Ackerman S J, Mafilios M S, and Polly D W, Jr. *Spine* 2002; 27:s94-s99). A 15,000-fold higher concentration of BMP-2 is required to induce bone in humans (1.5 mg/ml) than in cell culture (100 ng/ml). Thus, without a dramatic improvement in BMP-2 responsiveness, healthcare economics may severely limit translation of one of the most seminal discoveries related to osteoblast differentiation in the last 50 years from helping large numbers of patients.

Consequently, a further understanding of the complex regulation of BMP-2 during osteoblast differentiation and the cellular responsiveness to such important bone forming proteins is critical so that their effect can be enhanced or their required dose limited to a more affordable quantity of protein especially in the most challenging orthopaedic healing environment—posterolateral lumbar spine fusion.

Several years ago a novel intracellular LIM domain protein critical to fetal and post-natal bone formation was identified (Boden S D, Liu Y, Hair G A et al. *Endocrinology* 1998; 139:5125-34). Termed LIM Mineralization Protein (LMP-1) it was the first LIM domain protein to be directly associated with osteoblast differentiation. Blocking LMP-1 expression prevents osteoblast differentiation in vitro, suggesting a critical functional role of this novel intracellular protein. Leukocytes expressing the LMP-1 cDNA (via plasmid or adenoviral transduction) that are implanted into rabbits or athymic rats induce bone formation in bony and ectopic locations (Boden S D, Titus L, Hair G et al. *Spine* 1998; 23:2486-92). The feasibility of LMP-1 delivery by ex vivo gene therapy for spine fusion and bone defect applications in rabbits and primates is currently being evaluated. LMP-1 also has considerable potential as a local, regional, or systemic anabolic strategy for increasing bone density in patients with osteoporosis. However, before clinical applications can be seriously considered it will be critical to understand the mode of action of this protein.

Currently, three splice variants of LIM protein have been identified. These are termed LMP-1, LMP-2, and LMP-3. Human LMP-2 has a 119-base pair (bp) deletion between bp 325 and 444 and a 17-bp insertion at bp 444. The resulting derived protein contains 423 AA with the LIM domains intact and does not induce bone formation when overexpressed in ROB cultures. Human LMP-3 has the same 17 nucleotide insertion at bp 444, resulting in a shift in the reading frame that causes a stop codon to occur at bp 505-507. The resulting 153 AA protein does not have the LIM domains, but overexpression of LMP-3 induces bone formation in osteoblast cultures. Liu et al., *J Bone Miner Res.*, 17(3):406-14 (2002).

It was found that the LMP-1 and the LMP-3 proteins, but not the LMP-2 protein are capable of osteoinduction. The LMP-1 and the LMP-3 proteins possess a relatively short sequence comprising 45 amino acids, which is sufficient to exert an osteoinductive effect.

It has recently been described that this 45 amino acid sequence includes a binding site for a WW-2 domain of a Smurf1 protein. The binding between this osteoinductive amino acid sequence and the WW-2 domain of the Smurf1 protein leads to decreased degradation of Smad1 and Smad5 proteins which are known to mediate the osteogenic effect of the BMP-2 protein. However, more research is needed to provide a better understanding of the role of the LMP proteins in the osteogenesis, as well as the mechanisms by which the LMP proteins regulate osteogenesis. The better understanding of the LMP role may lead to more efficient and affordable therapies of bone defects.

SUMMARY OF INVENTION

The instant invention addresses these and the other needs in the prior art by providing, in one aspect, an osteogenic composition comprising a first amino acid sequence which is capable of being phosphorylated by CAMK2; a nucleic acid sequence encoding the first amino acid sequence; or a combination thereof. Additionally, the first amino acid sequence may comprise a second amino acid sequence which is capable of binding a Smurf1 protein. In different embodiments of the invention, the osteogenic composition may further comprise a BMP protein or a functional fragment thereof, a compound capable of decreasing an amount or an activity of calmodulin kinase 2, or both the BMP protein or the functional fragment thereof, and the compound capable of decreasing an amount or an activity of calmodulin kinase 2.

In another aspect, the invention provides an implant comprising the osteogenic composition according to any of the embodiments of the present invention.

In yet another aspect, the invention provides a method of inducing osteogenesis, the method comprising administering to a patient in need thereof the osteogenic composition according to any of the embodiments of the instant invention. In different embodiments, the ingredients of the osteogenic composition (e.g., the first amino acid sequence, the nucleic acid sequence encoding the first amino acid sequence, the BMP protein or the functional fragment thereof, the compound capable of decreasing the amount or the activity of calmodulin kinase 2) may be administered at the same time or at different times. The osteogenic composition may be administered to the surface of the defect, imbedded into an implant or delivered by any other means known in the art.

DETAILED DESCRIPTION OF PREFERRED EMBODIMENTS

For a better understanding of the invention, the following non-limiting definition shall apply throughout the instant disclosure.

As used herein a "functional fragment" of a protein is any fragment or portion of a protein which retains the characteristic of interest of the parent protein or peptide. As used herein "biologically active" means retaining that characteristic or property in question from the parent molecule. Accordingly, in the instant disclosure, the phrase "the functional fragment" of a BMP protein refers to the fragment of the BMP protein, which retains at least a portion of the osteogenic function of the BMP protein.

"A BMP protein" refers to an amino acid sequence at least 70% identical to the BMP-2 protein and retaining at least partially the osteogenic function of the BMP protein.

The methods of the present invention utilize routine techniques in the field of molecular biology. Basic texts disclosing general molecular biology methods include Sambrook et al., *Molecular Cloning, A Laboratory Manual* (3d ed. 2001) and Ausubel et al., *Current Protocols in Molecular Biology* (5th Ed. 2002).

The instant invention addresses these and the other needs in the prior art by providing novel compositions and methods of inducing osteogenesis.

As discussed above, the nucleic acid sequence for the LMP-3 protein has a 17 bp insertion. This insertion leads to a frame shift and a stop codon at nucleotides 505-507. The resulting LMP-3 protein is 153 amino acids long and is shown in SEQ. ID. NO. 1. As compared to the LMP-lt protein (SEQ. ID. NO. 2), which has its C-terminus truncated and comprises amino acids 1-223 of the LMP-1 protein, the LMP-3 protein contains the region of the LMP-1 protein and the LMP-lt protein capable inducing osteogenesis, and which includes a site capable of binding the WW-2 domain of the Smurf1 protein. This region is designated as SEQ. ID. NO. 3 (KPQKASAPAADPPRYTFAPSVSLNKTAR-PFGAPPPADSAPQQ), and the site capable of binding the WW-2 domain of the Smurf1 protein is designated as SEQ. ID. NO. 4 (GAPPPADSAP). In addition, the LMP-3 protein contains a unique amino acid sequence on its C-terminus. The inventors have discovered that this unique amino acid sequence (QNGCRPLTNSRSDRWSQMP, SEQ. ID. NO. 5) contains a site that is capable of being phosphorylated by (i.e., acts as a substrate for) calmodulin kinase 2, or CAMK2 (QNGCRPLTNSRSDRW, SEQ. ID. NO. 6).

Calmodulin is part of the classical inositol-phospholipid pathway found downstream of certain G-protein-linked receptors. Ligand binding to these receptors activates G-proteins, which in turn activate phospholipase C (PLC). PLC then cleaves phosphatidylinositolbisphosphate ($PIP_2$) to generate inositol-trisphosphate ($IP_3$) and diacylglycerol (DAG). While DAG activates protein kinase C (PKC), $IP_3$ induces the release of $Ca^{++}$ from the endoplasmic reticulum, which, in turn, binds to calmodulin to generate a Ca/calmodulin complex. Ca/calmodulin then activates kinases such as Ca/calmodulin-dependent protein kinase 2 (CaMK2). Calmodulin has been shown to bind Smads1-4 in vitro and in transfected cells in a calcium-dependent manner (Zimmerman et al., 1998). Calmodulin can bind to the N-terminal MH1 domain of both Smad1 and Smad2, but the exact role of calmodulin in TGF-β-related signaling is still uncertain. Linker region phosphorylation of Smad1 does not affect its oligomerization with Smad4 but inhibits nuclear entry of Smad1 and Smad4 complex, resulting in reduced levels of osteogenic response. Some data suggest a role of calmodulin in inhibiting activin signaling and stimulating BMP signaling. Thus, phosphorylation by CAMK2, may represent feed back regulation or cross-talk between BMP/Smad1 and Calmodulin/CAMK2 pathways. The observation that calmodulin may stimulate BMP signaling by interacting with Smad1 is consistent with other findings suggesting that $Ca^{++}$ signaling is important for ventral cell fate in embryonic development. For example, Kume et al. (1997) found that inhibiting $Ca^{++}$ release from the endoplasmic reticulum can suppress ventralization of *Xenopus* embryos after BMP4 overexpression. In addition, overexpression of CaMK2, which is normally activated by $Ca^{++}$/calmodulin, promotes ventral cell fate specification in *Xenopus*, and endogenous CaMK2 activity is highest on the prospective ventral side of blastula and gastrula stage *Xenopus* embryos (Kuhl et al., 2000). Thus, some of the available evidence suggests 'synergistic crosstalk between $Ca^{++}$/calmodulin and BMP-Smad signaling'. This crosstalk may be conserved between vertebrates and invertebrates since a $Ca^{++}$-gradient was found in *Drosophila* embryos with high levels on the dorsal side, coinciding with the peak Dpp activity (Cre'ton et al., 2000). Importantly, suppression of dorsally elevated $Ca^{++}$ levels results in embryos missing dorsal structures, suggesting that in *Drosophila*, $Ca^{++}$ signaling is required for proper dorsal development and could enhance Dpp signaling (Cre'ton et al., 2000).

Accordingly, in one aspect, the osteogenic composition comprises 1) a first amino acid sequence which is capable of being phosphorylated by CAMK2; 2) a nucleic acid sequence encoding the first amino acid sequence; or 3) a combination thereof.

A person of the ordinary skill in the art will recognize that a variety of amino acid sequences exists, which are capable of being phosphorylated by CAMK2. For example, in one embodiment, the first amino acid sequence may comprise SEQ. ID. NO. 5 (QNGCRPLTNSRSDRWSQMP) or SEQ. ID. NO. 6 (QNGCRPLTNSRSDRW). In other embodiments, the first amino acid comprises amino acid sequences which are capable of being phosphorylated by CAMK2 and which are not ordinarily present in the LMP-3 amino acid sequence. Suitable non-limiting examples of such amino acid sequences include SEQ. ID. NO. 7 (PLSRTLSVSS) and SEQ. ID. NO. 8 (PLARTLSVAGLPGKK).

In another embodiment, the first amino acid sequence further comprises a second amino acid sequence capable of binding the WW-2 domain of the Smurf1 protein. Generally, a consensus amino acid sequence binding a WW-2 domain is PPXY. It has been previously shown that the osteogenic region of the LMP-1 protein contains two potential binding sites for the WW-2 domain of the Smurf1 protein. These binding sites were designated as site A (ADPPRYTFAP, SEQ. TD. NO. 9) and site B (GAPPPADSAP, SEQ. ID. NO. 4). The experimental studies have revealed that site B is more important than site A. U.S. application Ser. No. 11/385,612 (Boden), filed on Mar. 21, 2006, incorporated herein by reference in its entirety. Accordingly, in one embodiment of the invention, the second amino acid sequence comprises the SEQ. ID. NO. 4. Further, experiments performed by the inventors indicate that the prolines of SEQ. ID. NO. 4 are necessary for the binding between SEQ. ID. NO. 4 and the WW-2domain of the Smurf1 protein. (APPLICATION DRAWN TO MOLECULAR INTERACTIONS BETWEEN LMP-1AND SMURF1 PROTEINS, 48170.00129, filed as U.S. application Ser. No. 11/607,348 and published as U.S. Patent Publication No. 2007/0190572, incorporated herein in its entirety). Thus, in another embodiment, the second amino acid sequence comprises SEQ. ID. NO. 10 (PPPAD).

The inventors further identified an amino acid sequence (FGAPPPADSAPQQNGCRPLTNSRSDRWSQMP, SEQ. ID. NO. 11; also referred to as Peptide 8) which contains the representative examples of the amino acid sequences which can serve as a substrate for CAMK2 protein and which can bind the Smurf1 protein. This amino acid sequence naturally occurs in the amino acid sequence of the LMP-3 protein. Accordingly, in one embodiment of the invention, the first amino acid sequence comprises SEQ. ID. NO. 11.

An amino acid sequence addition may include insertions of an amino- and/or carboxyl-terminal fusion ranging in length from one residue to one hundred or more residues, as well as internal intra-sequence insertions of single or multiple amino acid residues. Internal additions may range generally from about 1 to 20 amino acid residues, preferably from about 1 to 10 amino acid residues, more preferably from about 1 to 5 amino acid residues. An example of an amino-terminus or a carboxyl-terminus addition includes chimeric proteins comprising the amino-terminal or carboxyl-terminal fusion of the parent molecules with all or part of a transduction peptide or other conjugate moiety.

In yet another embodiment, the first amino acid sequence may further comprise a protein transduction domain (PTD) attached thereto. In one embodiment of the present invention, the PTD is derived from the HIV TAT protein. Non-limiting examples of suitable PTD sequences from the HIV TAT protein include SEQ. ID. NO. 12 (YGRKKRRQRRR) and SEQ. ID. NO. 13 (RKKRRQRRR).

In another embodiment, the composition comprising the desired nucleic acid sequence and/or the amino acid sequence may further comprise a transportation means. In one embodiment, the transportation means comprises liposomes or other compositions which increase the penetration of the desired amino acid and/or nucleic acid sequences into the cell of choice.

The invention also comprises chemically modified derivatives of the parent molecule(s) (such as, for example, the first amino acid sequence) in which the peptide is linked to a nonproteinaceous moiety (e.g., a polymer) in order to modify its properties. These chemically modified molecules are referred to herein as "derivatives." Such derivatives may be prepared by one skilled in the art given the disclosures herein. Conjugates may be prepared using glycosylated, non-glycosylated or de-glycosylated parent molecule(s) and suitable chemical moieties. Typically non-glycosylated molecules and water-soluble polymers will be used. Other derivatives encompassed by the invention include post-translational modifications (e.g., N-linked or O-linked carbohydrate chains, processing of N-terminal or C-terminal ends), attachment of chemical moieties to the amino acid backbone, and chemical modifications of N-linked or O-linked carbohydrate chains. The polypeptides may also be modified with a detectable label, such as an enzymatic, fluorescent, isotopic or affinity label to allow for detection and isolation of the protein peptide.

Water-soluble polymers are desirable because the protein or peptide to which the desired polymer is attached will not precipitate in an aqueous environment, such as a physiological environment. Preferably, the polymer will be pharmaceutically acceptable for the preparation of a therapeutic product or composition. One skilled in the art will be able to select the desired polymer based on such considerations as whether the polymer/protein conjugate will be used therapeutically and, if so, the therapeutic profile of the protein (e.g., duration of sustained release; resistance to proteolysis; effects, if any, on dosage; biological activity; ease of handling; degree or lack of antigenicity and other known effects of a water-soluble polymer on a therapeutic proteins).

Variants and/or derivatives may be screened to assess their physical properties in vitro and can be subsequently screened in vivo in the models described herein. It will be appreciated that such variant(s) will demonstrate similar properties to the unmodified molecule, but not necessarily all of the same properties and not necessarily to the same degree as the corresponding parent molecule.

In another embodiment, the composition may comprise a nucleic acid sequence encoding the first amino acid sequence. Such nucleic acid sequence may also serve as a template for production of the first amino acid sequence, as described below.

In other aspects, the osteogenic composition of the instant invention may comprise a Bone Morphogenic Protein ("BMP") or a functional fragment thereof, an agent capable of decreasing an amount or an activity of CAMK2, or any combination thereof.

In one embodiment, the osteogenic composition may comprise a nucleic acid sequence encoding the BMP protein or the functional fragment thereof. Non-limiting examples of the methods of manufacturing such nucleic acid sequences are described in details below.

Currently, multiple BMPs have been identified. They include, without limitations, BMP-2, BMP-4, BMP-5, BMP-6, and BMP-7 proteins. In one embodiment, the BMP protein is the BMP-2 protein. As discussed above, the BMP treatment is clinically effective but its monetary cost is relatively high, due, in part, to an unexpectedly high dose required for in vivo human treatment. Accordingly, in one embodiment of the invention, the dose of the BMP protein or the functional fragment thereof is below the dose of the BMP protein currently used for the treatment of the same bone defects. In selected embodiments, the dose of the BMP-2 protein is below 1.5 mg/mL, such as, for example, 0.5 mg/mL or 0.15 mg/mL or below 0.15 mg/mL.

Further, multiple agents exist which decrease the amount or the activity of CAMK2. Suitable non-limiting examples of such agents may be ordered from chemical/pharmaceutical companies which include, without limitations, Calbiochem, Inc. (La Jolla, Calif.). The suitable compounds include, without limitations, Lavendustin C (Calbiochem Catalog no. 234450), [Ala$^{286}$]-Ca$^{2+}$/Calmodulin Kinase II Inhibitor 281-301 (Calbiochem Catalog No. 208710), Calmodulin Kinase IINtide (Calbiochem Catalog No. 208920), Fasudil (5-Isoquinolinesulfonyl) homopiperazine (Calbiochem Catalog No. 371970), and other compounds listed in Calbiochem's catalog. Based on computational assignment of 3-D template structure of peptide 8 (SEQ. ID. NO. 11) and the selection of potential drug-like compounds using a suitable software, e.g., MODELER, DOCKING, and DISCOVERY modules software, followed by in silico screening, a person of ordinary skill in the art would be able to select additional suitable compounds, generally following the procedure as described, for example in 48170.00129. In one specific embodiment, such agent would be a small-molecule compound of low molecular weight, e.g., less than about 1,000 Da.

A person of the ordinary skill in the art will appreciate that the amino acid sequences, proteins and protein fragments described in the instant disclosure (including, without limitations, the first amino acid sequence, the second amino acid sequence, the BMP protein, or the functional fragment thereof) may be obtained by multiple methods. For example, the amino acid sequences of the osteogenic composition of the instant invention may be ordered from a manufacturer, such as, for example, New England Peptide, Inc. (Gardner, Mass.).

In another embodiment, the amino acid sequences of the instant invention can be synthesized by standard solid peptide synthesis (Barany, G. and Merrifield, R. B., The Peptides 2:1 284, Gross, E. and Meienhofer, J., Eds., Academic Press, New York) using tert-butyloxycarbonyl amino acids and phenylacetamidomethyl resins (Mitchell, A. R. et al., J. Org. Chem. 43:2845 2852 (1978)) or 9-fluorenylmethyloxycarbonyl amino acids on a polyamide support (Dryland, A. and Sheppard, R. C., J. Chem. So. Perkin Trans. I, 125 137 (1986)). Alternatively, synthetic peptides can be prepared by pepscan synthesis (Geysen, H. M. et al., J. Immunol. Methods 03:259 (1987); Proc. Natl. Acad. Sci. USA 81:3998 (1984)), Cambridge Research Biochemicals, Cambridge, U.K. or by standard liquid phase peptide synthesis.

In another embodiment, the amino acid sequences may be purified from a cellular source. The suitable sources include cells which natively express peptides containing those sequences as well as artificial expression system. The former include, without limitation, cultured osteoblasts and hMSCs. The purification techniques are well known in the art. One suitable method of purification is affinity chromatography. Essentially, in this technique, the cell extract is passed through a column impregnated with antibodies specifically recognizing the amino acid sequence of interest.

In yet another embodiment, the amino acid sequences and/or the nucleic acid sequences may be synthesized from recombinant sources. The mRNA and cDNA sequences of the LMP-3 protein (SEQ. ID. NO. 14), and the BMP protein, such as, for example, BMP-2 protein (SEQ. ID. NO. 15) are well known in the art and available, for example, from Genbank. Thus, the primers may be designed to multiply the nucleic acid sequence encoding the amino acid sequence of interest by PCR (if the template is cDNA) or RT-PCR (if the template is mRNA).

This nucleic acid sequence encoding the amino acid sequence of interest may be subcloned into a vector by methods well known in the art utilizing endonuclease and ligase properties. The vector may be either plasmid or viral vector. Suitable plasmid vectors include, without limitation, pUC18 and pUC 19. Suitable viral vectors include adenoviral vectors, adeno-associated vectors and baculoviral vectors. Additional examples of vectors are listed in catalogs of different manufacturers, including, without limitation, Promega Corp. (Madison, Wis.), incorporated herein by reference in its entirety.

Further, the vector may contain a promoter which directs the expression of the amino acid sequence of interest from the nucleic acid sequence. Suitable promoters include, without limitation, CMV, RSV, and TK. The vector containing the nucleic acid sequence encoding the amino acid sequence of interest is later introduced to host cells.

The choice of the host cell system depends largely on the type of the vector and the type of the promoter. In general, the host cells include, without limitations, prokaryotic, yeast, insect, and mammal cells. Essentially, the host cells should be selected based on the nature of the vector.

Suitable methods of introducing exogenous nucleic acid sequences are described in Sambrook and Russel, *Molecular Cloning: A Laboratory Manual* (3rd Ed., 2001), Cold Spring Harbor Press, NY. These methods include, without limitation, physical transfer techniques, such as, for example, microinjection or electroporation; transfections, such as, for example, calcium phosphate transfections; membrane fusion transfer, using, for example, liposomes; and viral transfer, such as, for example, the transfer using DNA or retroviral vectors. Other methods for introducing the nucleic acid sequences of the present invention into suitable cells, such as, for example, electroporation (see, e.g., Iversen et al., *Genetic Vaccines and Ther.* 3: 2-14 (2005)) will be apparent to a person of ordinary skill in the art. All such methods are within the scope of the present invention.

Depending on the type of the host cell, the codons of the nucleic acid sequences encoding the amino acid sequences of the instant invention can be selected for optimal expression in prokaryotic or eukaryotic systems. Host-vector systems include but are not limited to the following: bacteria transformed with bacteriophage DNA, plasmid DNA or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

The amino acid sequences used in the compositions and the methods of the instant invention can be purified or partially purified from cells comprising the vector, comprising the nucleic acid sequence encoding the amino acid sequence of interest (e.g., the first amino acid sequence or the BMP protein or the functional fragment of the BMP protein), using known purification processes such as gel filtration and ion exchange chromatography. Purification may also include affinity chromatography with agents known to bind the respective amino acid sequences.

Further, the amino acid sequences of interest may be tagged, as described in more details below. In one non-limiting example, the recombinant nucleic acid sequences are fused with a nucleic acid sequence encoding glutathione-S-transferase (GST). The GST-tag is often used to separate and purify proteins that contain the GST-fusion. GST-fusion proteins can be produced in *E. coli*, as recombinant proteins. The GST part binds its substrate, glutathione. Sepharose beads can be coated with glutathione, and such glutathione-sepharose beads bind GST-proteins. These beads are then washed, to remove contaminating bacterial proteins. Adding free glutathione to beads that bind purified GST-proteins will release the GST-protein in solution.

Once purified, the cleavage of the amino acid sequences of the instant invention into fragments of amino acid residues can be achieved using proteolytic enzymes such as thrombin or clostridiopeptidase B (clostripain). The exact time required for proteolysis varies with each preparation and markedly depends upon the batch of clostripain used. Therefore, the optimum time for a single cleavage must be determined for each combination of clostripain batch and the amino acid sequence used (e.g., the first amino acid sequence, the second amino acid sequence, the BMP protein or the functional fragment thereof). The protein fragments resulting from either thrombin or clostripain proteolysis may be further cleaved by digestion with trypsin, which cleaves on the carboxy terminus of lysine or arginine residues.

The sequence derived from proteolytic digestion may be identified using the Edman degradation method of protein sequencing. In addition, sequence analysis of the recombinant amino acid sequence of interest may be accelerated by using an automated liquid phase amino acid sequenator, thereby allowing for the analysis of picomolar quantities of the recombinant proteins containing up to 50 amino acid residues in length.

In one embodiment, the osteogenic composition of the instant invention may be formulated into a sustained-release formulation. Suitable sustained-release formulations include, without limitations, capsules, microspheres, particles, gels, coatings, matrices, wafers, pills or other pharmaceutical delivery compositions for containing one or more active ingredients. A depot may comprise a biopolymer. The biopolymer may provide for non-immediate release of the one or more active ingredients. Examples of suitable sustained release biopolymers include but are not limited to poly(alpha-hydroxy acids), poly(lactide-co-glycolide) (PLGA), polylactide (PLA), polyglycolide (PG), polyethylene glycol (PEG) conjugates of poly(alpha-hydroxy acids), polyorthoesters, polyaspirins, polyphosphagenes, collagen, starch, chitosans, gelatin, alginates, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, or combinations thereof.

In another embodiment, the osteogenic composition of the instant invention, including the osteogenic composition in the sustained release formulation, may be delivered as a bolus, or via an osmotic pump, an interbody pump, an infusion pump, implantable mini-pumps, a peristaltic pump, other pharmaceutical pumps, or a system administered locally by insertion of a catheter into, at or near a bone defect, the catheter being operably connected to a pharmaceutical delivery pump. It is understood that pumps can be internal or external as appropriate.

A person of the ordinary skill in the art will appreciate that the components of the osteogenic compositions of the instant invention may be delivered at the same time or at different time. For example, the components of the instant invention may be delivered via a pump connected to two or three reservoirs with different components of the osteogenic composition of the instant invention. In another embodiment, the components of the osteogenic composition may be formulated into different sustained-release formulations, wherein these formulations have different release profiles.

In yet another embodiment, the osteogenic composition according to any of the embodiments of the instant invention may be incorporated within an implant. Many devices of varying shapes and forms can be manufactured from cortical allograft tissue. Surgical implants such as pins, rods, screws, anchors, plates, and intervertebral spacers have all been made and used successfully in human surgery. The implant may be manufactured from bone, or bone particles or synthetic polymers or a combination thereof.

In one embodiment, the bone implant is derived from an the bones of the person being treated (autograft) or another individual of the same species but of different genotype (allograft). Allografts are used in repair of bone structures damaged by disease, trauma and surgery. Inadequate amounts of available autografts and the limited size and shape of a person's own bone makes allografts to be commonly used in reconstructive surgery. Using allograft tissue eliminates the need for a second operative site to remove autograft bone or tendon, reduces the risk of infection, and safeguards against temporary pain and loss of function at or near the secondary site. Moreover, allograft bone is a reasonable graft substitute for autologous bone and is readily available from cadavers. Allograft bone is essentially a load-bearing matrix comprised of cross-linked collagen, hydroxyapatite. Human allograft tissue widely used in orthopaedic surgery is strong, integrates with the recipient host bone, and can be shaped either by the surgeon to fit the specific defect or shaped commercially by a manufacturing process.

Allograft bone is available in two basic forms: cancellous and cortical. Cortical bone is a highly dense structure comprised of triple helix strands of collagen fiber reinforced with hydroxyapatite. The hydroxyapatite component is responsible for the high compressive strength and stiffness of bone while the collagen fiber component contributes to its elastic nature, as well as torsional, shear, and tensile strength. Cortical bone is the main load-bearing component of long bones in the human body.

In one embodiment, the implant comprises a textured graft, wherein the texturing comprises a plurality of closely spaced continuous or discrete protrusions.

In another embodiment, the implant comprises a combination of two cortical bone portions and a cancellous bone portion located between the cortical bone portions.

Optionally, the implant may be coated coated with a biopolymer seeded with periosteal cells harvested from either the graft recipient or from an allogenic or a xenogenic source.

In another embodiment, the implant is made up from demineralized bone powder or bone cement. In yet another embodiment, the implant may comprise synthetic polymers, including, without limitation, $\alpha$-hydroxy acids, such as polylactic acid, polyglycolic acid, enantioners thereof, co-polymers thereof, polyorthoesters, and combinations thereof.

In yet another embodiment, the implant is made up from ceramic materials. These materials preferably include porous calcium phosphate, such as, for example, hydroxyapatite (HA), tri-calcium phosphate (TCP) or any combination thereof, including, without limitations, approximately 30% HA and approximately 70% TCP.

Multiple methods exist for incorporating the osteogenic compositions of the instant invention into the implants. For example, in one embodiment, the implant is soaked in a solution comprising the osteogenic composition of the instant invention. In another embodiment, the implant is manufactured with a surfactant, as described, for example in U.S. Pat. No. 5,935,594 (Ringeisen), incorporated herein by reference in its entirety.

The therapeutic agents and compositions of the present invention are useful in treating subjects having bone disorders or compromised bone conditions. The bone disorder or compromised bone condition may be any disorder characterized by bone loss (osteopenia or osteolysis) or by bone damage or injury. Such bone conditions include but are not limited to broken bones, bone defects, bone transplant, bone grafts, bone cancer, joint replacements, joint repair, fusion, facet repair, bone degeneration, dental implants and repair, bone defects resulting from reconstructive surgeries, including, without limitations defects of the bones of the face (e.g., bones of the mouth, chin and jaw), bone marrow deficits and other conditions associated with bone and boney tissue.

Examples of bone defects include but are not limited to a gap, deformation or a non-union fracture in a bone.

Examples of bone degeneration include but are not limited to osteopenia or osteoporosis. In one embodiment, the bone defect is due to dwarfism.

The invention is also useful for joint replacement or repair wherein the joint is vertebral, knee, hip, tarsal, phalangeal, elbow, ankle, sacroiliac or other articulating/non-articulating joint.

Selected embodiment of the invention will now be further discussed in the following examples. The examples are illustrative only, and are not intended to limit the instant disclosure in any way.

EXAMPLES

Example 1

An Amino Acid Sequence Unique for LMP-3 Identifies a Site for CAMK2 Phosphorylation Sequence analysis of LMP variants by Scansite 2.0 module identifies an unique motif only in LMP-3. This motif (SEQ. ID. NO. 5) contains a sequence (SEQ. ID. NO. 6), which is most favored for phosphorylation by Calmodulin-dependent kinase 2.

Example 2

LMP-3 Competes with Smad1/5 for Smurf1 Binding

Smurf1 has been shown to bind bone-forming Smads in several studies. Smurf1 blots were probed with biotinylated LMP-3, Smad1 or Smad5 mixed with varying concentrations of competing un-labeled LMP proteins and binding was monitored by detecting biotin. The specific activity of biotin incorporation was normalized based on avidin-HABA assay.

Example 3

LMP-3-Derived Peptide 8 Inhibit Smurf1-Mediated Smad1 Ubiquitination

Based on in vito binding assays, LMP-3 derived Peptide 8 (SEQ. ID. NO. 11) is expected to mimic native LMP-1 and LMP-3, respectively, in blocking Smurf1 binding to Smad1 preventing its ubiquitination. As expected, Peptide 8 effectively blocked Smurf1-mediated Smad1 ubiquitination. This key confirmation lends support to our hypothesis that both the LMP-3 protein contains a motif that allows for interaction with Smurf1 resulting in effective rescue of Smad1 from ubiquitin-mediated proteasomal degradation.

Example 4

Recombinantly Purified Smad1 Undergoes CamKinase-Dependent Phosphorylation In Vitro Calmodulin kinase II ("Cam Kinase II" or "CaMK2") phosphorylated the purified recombinant Smad1 in an in vitro assay. The assay was performed in the presence of $Ca^{++}$ and Calmodulin with $^{32}P$-ATP. The reaction mixture without substrate Smad1 (control lane), showed no incorporation of $^{32}P$-label. Based on this result we conclude that Smad1 protein recombinantly expressed in *E. coli* and purified to homogeneity acts as substate for in vitro phosphorylation by Cam Kinase II. These phosphorylations are expected to occur in the central linker region of the Smad1 polypeptide.

Example 5

LMP-3 Undergoes CaMKinase II-Dependent Phosphorylation In Vitro

Purified recombinant LMP-1, LMP-2 and LMP-3, 10 ug each, were incubated with CaMK2 in the presence of $Ca^{++}$ and Calmodulin. Only LMP-3 was phosphorylated by Cam Kinase II whereas both LMP-1 and LMP-2 were not phosphorylated. We have thus defined a novel role for CaMK2 inhibition in the regulation and differential control of osteogenic Smad1. These observations have important implications for understanding the regulation vast range of Smad-mediated cellular events.

Example 6

LMP-3 Competes with Smad1 for In Vitro Phosphorylation by CaMK2

Smad1 undergoes phosphorylation by CaMK2 in $Ca^{++}$ and Calmodulin dependent fashion. In an in vitro assay we observed the dose dependent phosphorylation of Smad1 (tested at 0, 4, 8 and 16 ug of purified recombinant Smad1) by CamK2. The details of assay are mentioned in methods. Similarly, among the different isoforms of LMPs, only LMP-3 showed CamK2-mediated phosphorylation. When tested together, both Smad1 and LMP-3 acted as substrates to CamK2 in the same assay mixture.

Example 7

LMP-3 Derived Peptide 8 Mimics the Parent Molecule Function by Acting as Substrate to CamK2 Whereas the LMP-1-Derived Peptide 7 Fails to Act as Substrate for CamK2 in Vitro When Peptide 7 (FGAPPPADSAPQQNGQPLRPLVP-DASKQRLM, SEQ. ID. NO. 16) and Peptide 8 (SEQ. ID. NO. 11) were tested for their ability to act as substrate for CamKinase II-mediated phosphorylation, only Peptide 8 was phosphorylated as compared to Peptide 7, further confirming that only Peptide 8 contains the motif that interacted with CamKinase II for phosphorylation.

Example 8

Materials and Methods

The materials and methods of this example were used to obtain the results disclosed in the previous examples.

A. Bacterial Strains and Cloning of cDNAs in Bacterial Expression Vectors:

LMP-1, LMP-1t, LMP-2, LMP-3, Smad1 and Smad5 cDNAs were cloned into TAT-HA vector in XL1 blue host. LMP-1 mutants were generated using following primers:
hLMP1Mutant A forward primer:

5'-cgcccccgccgcggacgcagcacggtacacctttgcac-3' (SEQ. ID. NO. 17), hLMP1Mutant A reverse primer:

5'-gtgcaaaggtgtaccgtgctgctgccgcggcgggggcg-3,'(SEQ. ID. NO. 18), hLMP1Mutant B forward primer:
5'ggcccggcccttttggggcggcagcagcagctgacagcgccccgcaac-3' (SEQ. ID. NO. 19), hLMP1Mutant B reverse primer:
5'gttgcggggcgctgtcagctgctgctgccgccccaaaagggccgggcc-3' (SEQ. ID. NO. 20).

Smurf1 cDNA was cloned into pTrcHis vector (Invitrogen) and XL1 blue host. For generation of Smurf1ΔWW2 mutant the following primers were used: hSMURF1WW2 forward primer:
5'-gtgtgaactgtgatgaacttaatcaccagtgccaactc-3,'(SEQ. ID. NO. 21)

hSMURF1WW2 reverse primer
5'-gagttggcactggtgattaagttcatcacagttcacac-3'(SEQ. ID. NO. 22)

Mutagenesis was performed with Quikchange site-directed mutagenesis kit (Stratagene).

B. Expression and Purification of Recombinant Proteins:

E. coli grown at 37° C. to 0.6 $O.D_{600}$ was IPTG-induced at 200 uM and continued to grow 8 hrs. Cells were sonicated in lysis buffer (20 mM phosphate buffer, pH 7.0, 50 mM Tris-HCl, pH 7.5 and 5 M NaCl). The clarified lysate was applied onto Sephacryl S-100/S-200 columns (HiPrep 16×60) using AKTA FPLC system with Unicorn 4.0 software (Amersham Pharmacia Biotech). Fractions (2-4 ml) were collected and aliquots were analyzed by SDS-PAGE and western blotting. The fractions, identified by western blots were pooled, dialyzed and applied to $Ni^{++}$ affinity resin (Probond, Invitrogen). Non-specific proteins are washed off the column with 20 mM phosphate buffer, pH 6.0, urea (8 M), NaCl (50 mM) and imidazole (20 mM). Affinity-bound proteins were eluted with 20 mM phosphate buffer, pH 4.0, urea (8 M), NaCl (50 mM) and de-salted in centriprep devices (Amicon). Protein quantitation is performed with reagent (BioRad) using BSA as standard.

C. Cell Culture and Differentiation:

MSCs at passage 2 (Cambrex Bio Sciences) were grown at 37° C. in 5% $CO_2$ in MSCBM media supplemented with MSCGM Singlequots (Cambrex Bio Sciences), split at confluence, and plated at $3×10^4$ cells/well in 6-well dishes. The next day treatments were applied in the presence of 50 uM L-Ascorbic Acid 2-Phosphate and 5 mM β-glycerol phosphate (Sigma-Aldrich). Cells were transduced with adenoviral constructs in 0.5 ml serum-free medium. For differentiation, hMSCs at passage 4 were seeded at $3×10^4$ cells/well in a 6-well plate. The cells were infected with Ad35LMP-1 (1-10 pfu/cell) and incubated with or without BMP2 (100 ng/ml). The medium was replaced every 3-4 days and mineral deposition was observed after 2 weeks with Alizarin red.

D. SDS-PAGE and Western Blotting:

SDS-PAGE was performed using 10% gels and transferred to nitrocellulose membrane. The membrane was blocked with milk protein, incubated with specific antibody, washed with Tris Buffered Saline containing 0.1% Tween 20 (TBST), incubated with anti-rabbit goat IgG-linked to horseradish peroxidase (NEN). After washes, the chemiluminescent substrates were applied to the membrane and the signal is detected by exposing the membrane to X-ray film 30 sec.

E. Real-Time Reverse Transcription-Polymerase Chain Reaction (PCR):

Two μg of total RNA was reverse transcribed in a 100 μl volume containing 50 mM KCl, 10 mM Tris, pH 8.3, 5.5 mM $MgCl_2$, 0.5 mM each dNTPs, 0.125 μM random hexamer, 40 units RNase Inhibitor, and 125 units MultiScribe (Applied Biosystems). Samples were incubated for 10 min at 25° C., 30 minutes at 48° C., and then 5 min. at 95° C. Real-time PCR was performed on the resulting cDNA in a total volume of 25 μl containing 12.5 μl of 2×SYBR Green PCR Master Mix (Applied Biosystems), and 0.8 μM each primer. The PCR parameters used were 2 min at 50° C., 10 min. at 95° C., and 45 cycles of 95° C. for 15 sec. followed by 1 min at 62° C.

F. Slot-Blot Assay:

Twenty μl of purified Smurf1 (50 μg/ml) was blotted onto nitrocellulose in slot blot wells and wells were blocked with 0.5% tween 20 in TBST for 30 min. Biotinylated-ligand (LMP-1, LMP-2, LMP-3, Smad1 or Smad5) was mixed with varying concentrations of competing proteins or peptides and incubated in slot blot wells with Smurf1 for 90 min. Wells were washed and the blots were blocked with TBST containing 0.5% tween 20. The blots were then incubated with HRP-labeled avidin for 1 hr. After washes the blots were incubated with ECL substrate solution and the membranes were exposed to X-ray film for signal detection.

G. Ubiquitination In Vitro:

Purified Smad1 (100 ng), in ubiquitination buffer (50 μM Tris-HCl pH 8.0, 5 mM $MgCl_2$, 0.5 mM dithiothreitol (DTT), 2 mM NaF, and 3 μM okadaic acid), was incubated with E1, E2 ligases and Smurf1 (E3 ligase) with or without recombinant LMP-1 protein. The reaction mixture also contained 2 mM ATP, labeled ubiquitin (150 μM), ubiquitin aldehyde (5 μM), and creatine kinase-ATP generating system. The ubiquitin aldehyde was included to prevent hydrolysis of polyubiquitin chains. The reaction mixture (50 μl) was incubated up to 3 hr at 37° C. Aliquots at various time points were taken for SDS-PAGE and western blotting using specific antibody for Smad and/or ubiquitin.

H. CaMK2 Assay:

CaMK2 activity was measured according to Johnson et al. (Johnson et al., 1998). The protein samples were stored in assay buffer (115 mmol/l KCl, 5 mmol/15,5'-diBrBAPTA, 2.1 mmol/l $CaCl_2$, 5.75 mmol/l $MgCl_2.6H_2O$, 2.2 μmol/l PKI, 75 μmol/l genestein, 200 μmol/l PKCΨ, 240 mmol/l β-glycerophosphate, 120 mmol/l para-nitrophenyl phosphate, 1 mg/ml of each protease inhibitor aprotinin, trypsin/chymotrypsin inhibitors, chymostatin, leupeptin, pepstatin and 23 mmol/l HEPES, pH 6.8) at −80° C. until use. After thawing, the reaction was started by adding 10 ug autocamtide-2 in each sample as a specific substrate for CamK2 and 0.25 μCi $[\gamma-^{32}P]$/ml (Amersham Pharmacia Biotech). After 30 min at 37° C., assays were stopped by adding tricine sample buffer (BioRad Laboratories, Hercules, Calif., USA) and samples were electrophoresed on precast Tris-Tricine polyacrylamide gel (BioRad). Following electrophoresis the gel was fixed for 60 min in 0.2% gluteraldehyde and 0.2 mol/l sodium acetate in 30% ethanol, dried and exposed to a phosphor screen for 12 h at −80° C.

Every patent and non-patent publication cited in the instant disclosure, except U.S. application Ser. No. 10/806,915 and U.S. Provisional Application No. 60/456,551, is incorporated into the disclosure by reference to the same effect as if every publication is individually incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

The invention claimed is:

1. An osteogenic composition comprising:
a first amino acid sequence capable of being phosphorylated by CAMK2, wherein the first amino acid sequence is SEQ. ID. NO. 11.

2. The osteogenic composition of claim 1, further comprising a PTD domain.

3. The osteogenic composition of claim 2, wherein the PTD domain is identical to SEQ. ID. NO 12 or SEQ. ID. NO. 13.

4. The osteogenic composition of claim 1, which is in a sustained-release formulation.

5. An implant comprising the osteogenic composition of claim 1.

6. The implant of claim 5, which is selected from pins, rods, screws, anchors, plates, intervertebral spacers, and any combinations thereof.

* * * * *

SEQUENCE LISTING

<160> NUMBER OF SEQ ID NOS: 22

<210> SEQ ID NO 1
<211> LENGTH: 153
<212> TYPE: PRT
<213> ORGANISM: Homo sapiens

<400> SEQUENCE: 1

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
        115                 120                 125

Pro Gln Gln Asn Gly Cys Arg Pro Leu Thr Asn Ser Arg Ser Asp Arg
130                 135                 140

Trp Ser Gln Met Pro Ala Ser Ser Gly
145                 150

<210> SEQ ID NO 2
<211> LENGTH: 223
<212> TYPE: PRT
<213> ORGANISM: Homo sapiens

<400> SEQUENCE: 2

Met Asp Ser Phe Lys Val Val Leu Glu Gly Pro Ala Pro Trp Gly Phe
1               5                   10                  15

Arg Leu Gln Gly Gly Lys Asp Phe Asn Val Pro Leu Ser Ile Ser Arg
            20                  25                  30

Leu Thr Pro Gly Gly Lys Ala Ala Gln Ala Gly Val Ala Val Gly Asp
        35                  40                  45

Trp Val Leu Ser Ile Asp Gly Glu Asn Ala Gly Ser Leu Thr His Ile
    50                  55                  60

Glu Ala Gln Asn Lys Ile Arg Ala Cys Gly Glu Arg Leu Ser Leu Gly
65                  70                  75                  80

Leu Ser Arg Ala Gln Pro Val Gln Ser Lys Pro Gln Lys Ala Ser Ala
                85                  90                  95

Pro Ala Ala Asp Pro Pro Arg Tyr Thr Phe Ala Pro Ser Val Ser Leu
            100                 105                 110

Asn Lys Thr Ala Arg Pro Phe Gly Ala Pro Pro Ala Asp Ser Ala
        115                 120                 125

Pro Gln Gln Asn Gly Gln Pro Leu Arg Pro Leu Val Pro Asp Ala Ser
130                 135                 140

Lys Gln Arg Leu Met Glu Asn Thr Glu Asp Trp Arg Pro Arg Pro Gly
145                 150                 155                 160

-continued

```
Thr Gly Gln Ser Arg Ser Phe Arg Ile Leu Ala His Leu Thr Gly Thr
            165                 170                 175
Glu Phe Met Gln Asp Pro Asp Glu Glu His Leu Lys Lys Ser Ser Gln
        180                 185                 190
Val Pro Arg Thr Glu Ala Pro Ala Pro Ala Ser Ser Thr Pro Gln Glu
    195                 200                 205
Pro Trp Pro Gly Pro Thr Ala Pro Ser Pro Thr Ser Arg Pro Pro
210                 215                 220

<210> SEQ ID NO 3
<211> LENGTH: 42
<212> TYPE: PRT
<213> ORGANISM: Homo sapiens

<400> SEQUENCE: 3

Lys Pro Gln Lys Ala Ser Ala Pro Ala Ala Asp Pro Pro Arg Tyr Thr
1               5                   10                  15
Phe Ala Pro Ser Val Ser Leu Asn Lys Thr Ala Arg Pro Phe Gly Ala
            20                  25                  30
Pro Pro Pro Ala Asp Ser Ala Pro Gln Gln
        35                  40

<210> SEQ ID NO 4
<211> LENGTH: 10
<212> TYPE: PRT
<213> ORGANISM: Homo sapiens

<400> SEQUENCE: 4

Gly Ala Pro Pro Pro Ala Asp Ser Ala Pro
1               5                   10

<210> SEQ ID NO 5
<211> LENGTH: 19
<212> TYPE: PRT
<213> ORGANISM: Homo sapiens

<400> SEQUENCE: 5

Gln Asn Gly Cys Arg Pro Leu Thr Asn Ser Arg Ser Asp Arg Trp Ser
1               5                   10                  15
Gln Met Pro

<210> SEQ ID NO 6
<211> LENGTH: 15
<212> TYPE: PRT
<213> ORGANISM: Homo sapiens

<400> SEQUENCE: 6

Gln Asn Gly Cys Arg Pro Leu Thr Asn Ser Arg Ser Asp Arg Trp
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Leu Ser Arg Thr Leu Ser Val Ser Ser
1               5                   10
```

```
<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Pro Leu Ala Arg Thr Leu Ser Val Ala Gly Leu Pro Gly Lys Lys
 1               5                  10                  15

<210> SEQ ID NO 9
<211> LENGTH: 10
<212> TYPE: PRT
<213> ORGANISM: Homo sapiens

<400> SEQUENCE: 9

Ala Asp Pro Pro Arg Tyr Thr Phe Ala Pro
 1               5                  10

<210> SEQ ID NO 10
<211> LENGTH: 5
<212> TYPE: PRT
<213> ORGANISM: Homo sapiens

<400> SEQUENCE: 10

Pro Pro Pro Ala Asp
 1               5

<210> SEQ ID NO 11
<211> LENGTH: 31
<212> TYPE: PRT
<213> ORGANISM: Homo sapiens

<400> SEQUENCE: 11

Phe Gly Ala Pro Pro Ala Asp Ser Ala Pro Gln Gln Asn Gly Cys
 1               5                  10                  15

Arg Pro Leu Thr Asn Ser Arg Ser Asp Arg Trp Ser Gln Met Pro
                20                  25                  30

<210> SEQ ID NO 12
<211> LENGTH: 11
<212> TYPE: PRT
<213> ORGANISM: Human immunodeficiency virus

<400> SEQUENCE: 12

Tyr Gly Arg Lys Lys Arg Arg Gln Arg Arg Arg
 1               5                  10

<210> SEQ ID NO 13
<211> LENGTH: 9
<212> TYPE: PRT
<213> ORGANISM: Human immunodeficiency virus

<400> SEQUENCE: 13

Arg Lys Lys Arg Arg Gln Arg Arg Arg
 1               5

<210> SEQ ID NO 14
<211> LENGTH: 1686
<212> TYPE: DNA
<213> ORGANISM: Homo sapiens
```

<400> SEQUENCE: 14

```
cgacgcagag cagcgccctg gccgggccaa gcaggagccg gcatcatgga ttccttcaag      60
gtagtgctgg aggggccagc accttggggc ttccggctgc aaggggggcaa ggacttcaat    120
gtgcccctct ccatttcccg gctcactcct gggggcaaag cggcgcaggc cggagtggcc    180
gtgggtgact gggtgctgag catcgatggc gagaatgcgg gtagcctcac acacatcgaa    240
gctcagaaca agatccgggc ctgcggggag cgcctcagcc tgggcctcag cagggcccag    300
ccggttcaga gcaaaccgca gaaggcctcc gccccgccg cggaccctcc gcggtacacc      360
tttgcaccca cgtctccct caacaagacg gcccggccct tggggcgcc cccgcccgct       420
gacagcgccc cgcaacagaa tgggtgcaga ccctgacaa acagccgctc cgaccgctgg       480
tcccagatgc cagcaagcag cggctgatgg agaacacaga ggactggcgg ccgcggccgg    540
ggacaggcca gtcgcgttcc ttccgcatcc ttgcccacct cacaggcacc gagttcatgc    600
aagacccgga tgaggagcac ctgaagaaat caagccaggt gcccaggaca gaagcccag     660
ccccagcctc atctacaccc caggagccct ggcctggccc taccgccccc agccctacca    720
gccgcccgcc ctgggctgtg accctgcgt ttgccgagcg ctatgccccg gacaaaaacga    780
gcacagtgct gacccggcac agccagccgg ccacgcccac gccgctgcag agccgcacct    840
ccattgtgca ggcagctgcc ggaggggtgc caggaggggg cagcaacaac ggcaagactc    900
ccgtgtgtca ccagtgccac aaggtcatcc ggggccgcta cctggtggcg ttgggccacg    960
cgtaccaccc ggaggagttt gtgtgtagcc agtgtgggaa ggtcctggaa gagggtggct   1020
tctttgagga agggcgcc atcttctgcc caccatgcta tgacgtgcgc tatgcaccca    1080
gctgtgccaa gtgcaagaag aagattacag gcgagatcat gcacgccctg aagatgacct   1140
ggcacgtgca ctgctttacc tgtgctgcct gcaagacgcc catccggaac agggccttct   1200
acatggagga gggcgtgccc tattgcgagc gagactatga aagatgtttt ggcacgaaat   1260
gccatggctg tgacttcaag atcgacgctg gggaccgctt cctggaggcc ctgggcttca   1320
gctggcatga cacctgcttc gtctgtgcga tatgtcagat caacctggaa ggaaagacct   1380
tctactccaa gaaggacagg cctctctgca agagccatgc cttctctcat gtgtgagccc   1440
cttctgccca cagctgccgc ggtggcccct agcctgaggg gcctggagtc gtggccctgc   1500
atttctgggt agggctggca atggttgcct taaccctggc tcctggcccg agcctggggc   1560
tccctgggcc ctgccccacc caccttatcc tcccacccca ctccctccac caccacagca   1620
caccggtgct ggccacacca gccccctttc acctccagtg ccacaataaa cctgtaccca   1680
gctgtg                                                              1686
```

<210> SEQ ID NO 15
<211> LENGTH: 3150
<212> TYPE: DNA
<213> ORGANISM: Homo sapiens

<400> SEQUENCE: 15

```
ccacaaaggg cacttggccc cagggctagg agagcgaggg gagagcacag ccacccgcct      60
cggcggcccg ggactcggct cgactcgccg gagaatgcgc ccgaggacga cggggcgcca    120
gagccgcggt gctttcaact ggcgagcgcg aatgggggtg cactggagta aggcagagtg    180
atgcggggg gcaactcgcc tggcaccgag atcgccgccg tgcccttccc tggacccggc    240
gtcgcccagg atggctgccc cgagccatgg gccgcggcg agctagcgcg gagcgcccga    300
ccctcgaccc ccgagtcccg gagccggccc cgcgcggggc cacgcgtccc tcgggcgctg    360
```

```
gttcctaagg aggacgacag caccagcttc tcctttctcc cttcccttcc ctgccccgca      420
ctcctccccc tgctcgctgt tgttgtgtgt cagcacttgg ctggggactt cttgaacttg      480
cagggagaat aacttgcgca ccccactttg cgccggtgcc tttgcccag cggagcctgc       540 ttcgccatct ccgagcccca ccgcccctcc actcctcggc cttgcccgac actgagacgc      600
tgttcccagc gtgaaaagag agactgcgcg gccggcaccc gggagaagga ggaggcaaag      660
aaaaggaacg acattcggt ccttgcgcca ggtcctttga ccagagtttt tccatgtgga       720
cgctctttca atggacgtgt ccccgcgtgc ttcttagacg gactgcggtc tcctaaaggt      780
cgaccatggt ggccgggacc cgctgtcttc tagcgttgct gcttcccag gtcctcctgg       840 gcggcgcggc tggcctcgtt ccggagctgg gccgcaggaa gttcgcggcg cgtcgtcgg       900 gccgcccctc atcccagccc tctgacgagg tcctgagcga gttcgagttg cggctgctca      960
gcatgttcgg cctgaaacag agacccaccc ccagcaggga cgccgtggtg ccccccctaca    1020 tgctagacct gtatcgcagg cactcaggtc agccgggctc acccgcccca gaccaccggt    1080
tggagagggc agccagccga gccaacactg tgcgcagctt ccaccatgaa gaatctttgg    1140
aagaactacc agaaacgagt gggaaaacaa cccggagatt cttctttaat ttaagttcta    1200
tccccacgga ggagtttatc acctcagcag agcttcaggt tttccgagaa cagatgcaag    1260
atgctttagg aaacaatagc agtttccatc accgaattaa tatttatgaa atcataaaac    1320
ctgcaacagc caactcgaaa ttccccgtga ccagacttt ggacaccagg ttggtgaatc    1380
agaatgcaag caggtgggaa agttttgatg tcacccccgc tgtgatgcgg tggactgcac    1440
agggacacgc caaccatgga ttcgtggtgg aagtggccca cttggaggag aaacaaggtg    1500
tctccaagag acatgttagg ataagcaggt ctttgcacca agatgaacac agctggtcac    1560
agataaggcc attgctagta acttttggcc atgatggaaa agggcatcct ctccacaaaa    1620
gagaaaaacg tcaagccaaa cacaaacagc ggaaacgcct taagtccagc tgtaagagac    1680 acccttgta cgtggacttc agtgacgtgg ggtggaatga ctggattgtg gctcccccgg    1740
ggtatcacgc cttttactgc cacggagaat gcccttttcc tctggctgat catctgaact    1800
ccactaatca tgccattgtt cagacgttgg tcaactctgt taactctaag attcctaagg    1860
catgctgtgt cccgacagaa ctcagtgcta tctcgatgct gtaccttgac gagaatgaaa    1920
aggttgtatt aaagaactat caggacatgg ttgtggaggg ttgtgggtgt cgctagtaca    1980
gcaaaattaa atacataaat atatatatat atatatattt tagaaaaaag aaaaaaacaa    2040
acaaacaaaa aaacccccacc ccagttgaca ctttaatatt tcccaatgaa gactttatttt   2100 atggaatgga atgaaaaaa aaacagctat tttgaaaata tatttatatc tacgaaaaga     2160
agttgggaaa acaaatattt taatcagaga attattcctt aaagatttaa aatgtatttaa    2220 gttgtacatt ttatatgggt tcaaccccag cacatgaagt ataatggtca gatttatttt    2280
gtatttattt actattataa ccactttta ggaaaaaat agctaatttg tatttatatg      2340
taatcaaaag aagtatcggg tttgtacata atttttccaaa aattgtagtt gttttcagtt   2400
gtgtgtattt aagatgaaaa gtctacatgg aaggttactc tggcaaagtg cttagcacgt    2460 ttgcttttt gcagtgctac tgttgagttc acaagttcaa gtccagaaaa aaaaagtgga    2520
taatccactc tgctgacttt caagattatt atattattca attctcagga atgttgcaga    2580
gtgattgtcc aatccatgag aatttacatc cttattaggt ggaatatttg gataagaacc    2640
agacattgct gatctattat agaaactctc ctcctgcccc ttaatttaca gaaagaataa    2700
agcaggatcc atagaaataa ttaggaaaac gatgaacctg caggaaagtg aatgatggtt    2760
```

-continued

```
tgttgttctt ctttcctaaa ttagtgatcc cttcaaaggg gctgatctgg ccaaagtatt    2820
caataaaacg taagatttct tcattattga tattgtggtc atatatattt aaaattgata    2880
tctcgtggcc ctcatcaagg gttggaaatt tatttgtgtt ttacctttac ctcatctgag    2940
agctctttat tctccaaaga acccagtttt ctaactttt gcccaacacg cagcaaaatt     3000
atgcacatcg tgttttctgc ccaccctctg ttctctgacc tatcagcttg cttttctttc    3060
caaggttgtg tgtttgaaca catttctcca aatgttaaac ctatttcaga taataaatat    3120
caaatctctg gcatttcatt ctataaagtc                                     3150
```

<210> SEQ ID NO 16
<211> LENGTH: 31
<212> TYPE: PRT
<213> ORGANISM: Homo sapiens

<400> SEQUENCE: 16

Phe Gly Ala Pro Pro Ala Asp Ser Ala Pro Gln Gln Asn Gly Gln
 1               5                  10                  15

Pro Leu Arg Pro Leu Val Pro Asp Ala Ser Lys Gln Arg Leu Met
            20                  25                  30

<210> SEQ ID NO 17
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
cgcccccgcc gcggacgcag cacggtacac ctttgcac                            38

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
gtgcaaaggt gtaccgtgct gcgtccgcgg cggggggcg                            38

<210> SEQ ID NO 19
<211> LENGTH: 47
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
ggcccggccc tttggggcgg cagcagcagc tgacagcgcc ccgcaac                  47

<210> SEQ ID NO 20
<211> LENGTH: 47
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20 gttgcgggg ctgtcagct gctgctgccg ccccaaaggg ccggggcc                   47

-continued

```
<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
gtgtgaactg tgatgaactt aatcaccagt gccaactc                              38

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
gagttggcac tggtgattaa gttcatcaca gttcacac                              38
```